United States Patent [19]

Burstein et al.

[11] 4,336,691

[45] Jun. 29, 1982

[54] CRYOJET RAPID FREEZING APPARATUS

[75] Inventors: Neal L. Burstein, Stanford; David M. Maurice, Atherton, both of Calif.

[73] Assignee: The Board of Trustees of the Leland Stanford Junior University, Stanford, Calif.

[21] Appl. No.: 103,216

[22] Filed: Dec. 13, 1979

[51] Int. Cl.$^3$ ............................................. F25D 17/02
[52] U.S. Cl. ........................................ 62/64; 62/78; 62/514 R
[58] Field of Search .................... 62/514 R, 78, 64, 55

[56] References Cited

U.S. PATENT DOCUMENTS

| | | | |
|---|---|---|---|
| 3,206,938 | 9/1965 | Damsz | 62/55 |
| 3,206,939 | 9/1965 | Wilson | 62/55 |
| 3,734,123 | 5/1973 | Pomerantz | 137/392 |
| 4,030,314 | 6/1977 | Strehler | 62/55 |
| 4,059,424 | 11/1977 | Bentz | 62/49 |
| 4,068,495 | 1/1978 | Meer et al. | 62/514 R |
| 4,107,937 | 8/1978 | Chmiel | 62/78 |

OTHER PUBLICATIONS

Baker, J.R.J. et al., "A technique for electron microscope autoradiography (and X-ray microanalysis) of diffusible substances using freeze-dried fresh frozen sections", *Journal of Microscopy*, vol. 108, pt. 3, Dec. 1967, pp. 307–315.
Bald, W. B. et al., "A device for the rapid freezing of biological specimens under precisely controlled and reproducible conditions", *Journal of Microscopy*, vol. 112, pt. 1, Jan. 1978, pp. 3–15.
Bullivant, S., "Freeze Substitution and Supporting Techniques", Laboratory Investigation, vol. 14, No. 6, 1965 pp. 440–457.
Kent Christensen, A., "Frozen Thin Sections of Fresh Tissue for Electron Microscopy, with a Description of Pancreas and Liver", *The Journal of Cell Biology*, vol. 51, 1971, pp. 772–804.
Costello, M. J. et al., "The direct measurement of temperature changes within freeze-fracture specimens during rapid quenching in liquid coolants", *Journal of Microscopy*, vol. 112, pt. 1, Jan. 1978, pp. 17–37.
Dikstein, S. et al., "The Metabolic Basis to the Fluid Pump in the Cornea", *J. Physiol.*, 221, pp. 29–41.
Heuser, J. E. et al., "Preservation of Synaptic Structure by Rapid Freezing", *Cold Spring Harbor Symp.* 1975, pp. 17–24.
Hodson, S., "Inadequacy of Aldehyde fixatives in preserving the ultrastructure of corneal endothelium in rabbit and monkey", *Exp. Eye Res.*, 1968, 7:221–224.
Johnson, I. T. et al., "The ultrastructure of rat intestinal epithelium as revealed by cryoultramicrotomy and transmission electron microscopy, *Micron*, 1977, 8: 139–143.
Mazur, P., "The Role of Intracellular Freezing in the Death of Cells Cooled of Supraoptimal Rates", *Cryobiology*, 14, (1977), pp. 251–272.
Moor, H., "Recent Progress in the Freeze-etching Technique", *Phil. Trans. Roy. Soc. Lond.* 261:121–131 (1971).
Rebhun, L. I., "Freeze-subscription and freeze-drying", Principles and Techniques of Electron Microscopy, vol. 2, M. A. Hayad (ed.), Van Nostrand-Reinhold, N.Y., pp. 3–49 (1972).
Van Harreveld, A. et al., "Electron Microscopy after Rapid Freezing on a metal surface and substitution fixation", *Anat. Rec.*, 149:381–386 (1964).
Van Zyl, J. et al., "Freeze Substitution of Plant and Animal Tissue for the localization of Water-soluble Compounds by Electron Probe Microanalysis", *Micron*, 7:213–224 (1976).

*Primary Examiner*—Ronald C. Capossela
*Attorney, Agent, or Firm*—Browdy and Neimark

[57] ABSTRACT

This invention relates to the freezing of biological tissues in a rapid manner in order to prevent the formation of ice crystals in tissue surface layers. The apparatus consists of a reservoir containing a liquid quenchant near its melting temperature, a jet nozzle for delivery of the liquid, and a means of preventing liquid from contacting tissue until it has reached low temperature and a uniform flow has been established.

Fixation occurs within a small fraction of a second near the tissue surface, so that small polar molecules and ions can be prevented from diffusion during and after fixation, and their position at the time of fixation can be later determined. The process is applicable to freeze-fixation, freeze-preservation, freeze-fracture, and to rapid cooling of small areas of surfaces when it is desired to limit crystal formation by establishing a high rate of cooling.

17 Claims, 6 Drawing Figures

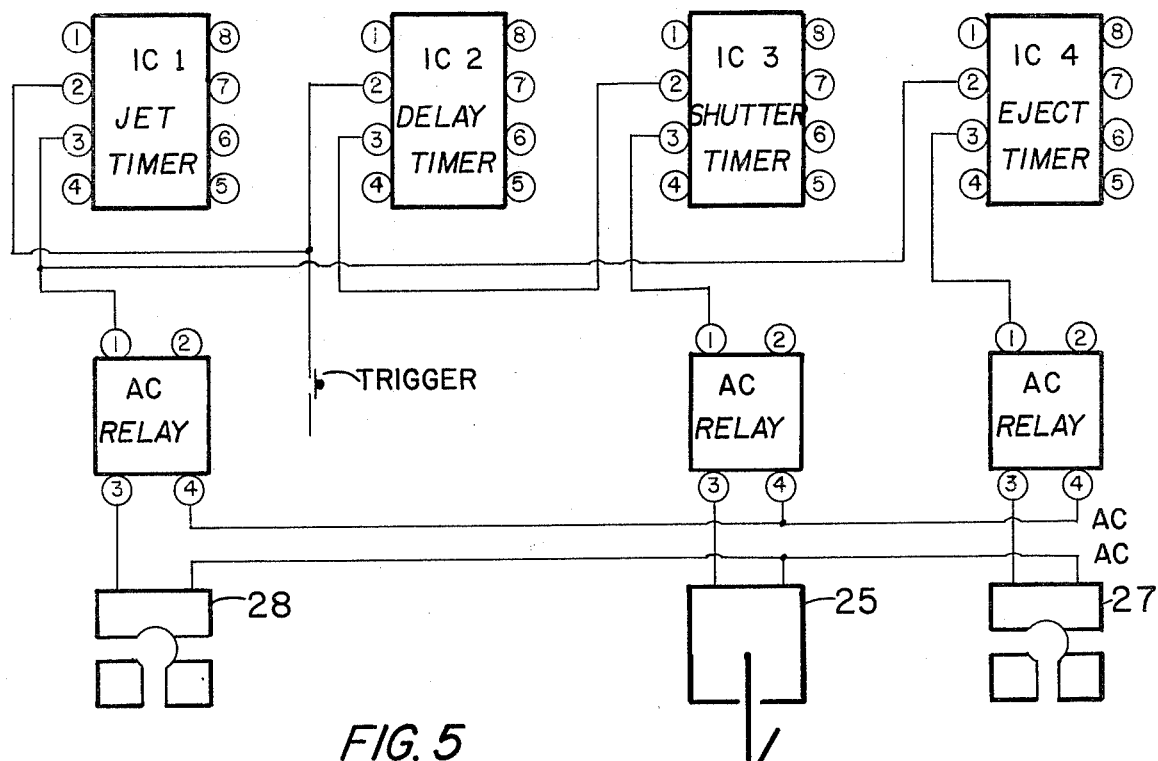
FIG. 5
FIG. 6
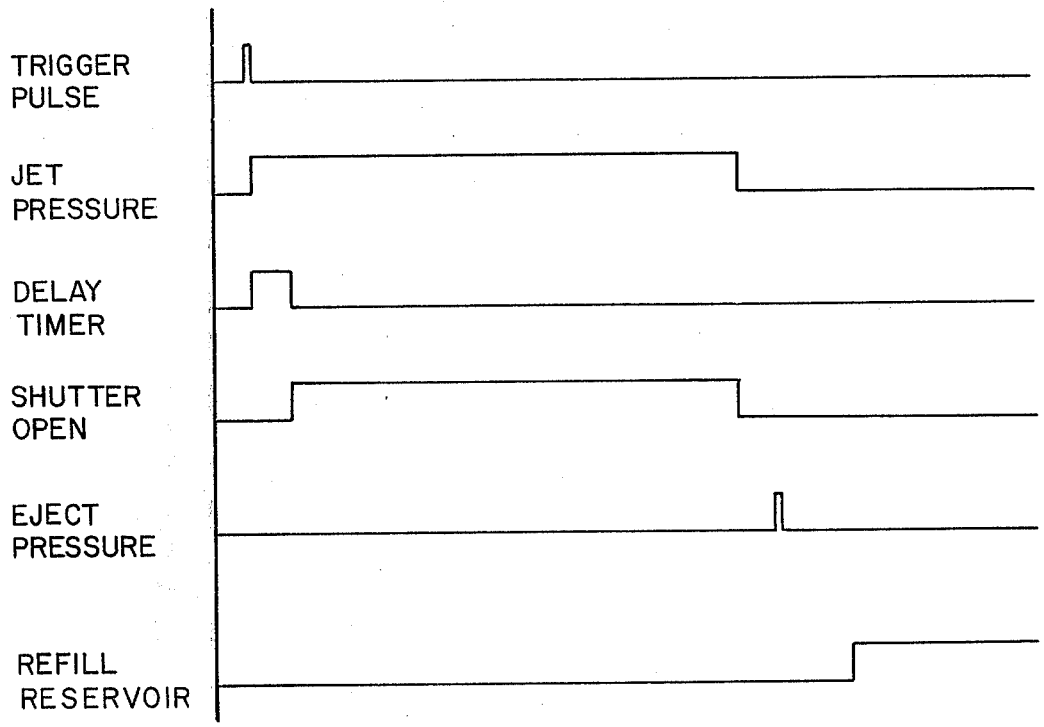

CRYOJET RAPID FREEZING APPARATUS

The invention described herein was made in the course of work under a grant or award from the U.S. Department of Health, Education, and Welfare.

FIELD OF INVENTION

The invention and process relate to the ultrarapid freezing of small surface areas of large or irregular objects such as biological tissues, in preparation for fixation for microscopical analysis and in preservation for later thawing and reconstitution or revitalization.

BACKGROUND OF INVENTION

Heretofore, biological tissues when frozen developed ice crystals large enough to destroy cellular function and impede viewing by electron microscopy. This could be avoided only where the tissue was either extremely small, or prepared in special cryoprotective media. Various devices developed in an attempt to freeze portions of large tissues without cryoprotective agents included: metal anvils cooled to cryogenic temperatures and brought into contact with tissue surfaces; gaseous sprays; carbon dioxide sprays in pressurized liquid form or in solid form; and sprays of liquified nitrogen, oxygen, or helium. While liquid nitrogen and liquid helium are considered standard in the art for achieving low temperatures conveniently, they do not cool as rapidly as generally expected, since they form an envelope of gaseous insulation immediately surrounding the specimen surface. In like manner, fluid baths simply brought in contact with surfaces can have a barrier layer impeding cooling, as taught by Alger et. al. (U.S. Pat. No. 4,068,495). For very small objects such as individual seeds or blood cells, direct cooling in quenchant liquids held near their melting temperature has been the most successful technique for rapid freezing.

The use of chemical agents including fixatives and chemical media can distort the normal spatial relationships between cellular and tissue components, and can allow the diffusion of substances for a period of many minutes before fixation can occur. Even after conventional means of fixation, small ionic forms can diffuse readily and be lost to analysis.

OBJECTS OF INVENTION

Accordingly several objects of our invention are:

1. That it freeze tissues rapidly enough to prevent large ice crystal formation near the surface of the tissues;
2. That it freeze areas of tissues which are too large to introduce into an apparatus;
3. That it freeze surfaces of objects much more rapidly than previously possible for very thin layers near the surface of the objects;
4. That it immobilize cellular organelles and cells within tissues so that they may be viewed as they were at nearly one instant of time without having been subjected to chemical techniques before immobilization;
5. That it immobilize small polar ions at the time of fixation so that they do not diffuse and can be later studied and measured by existing techniques;
6. That the equipment and process occupy a small area compared with earlier and less suitable techniques;
7. That the process and apparatus be simple enough to allow facility of tissue fixation;
8. That the process and device be capable of wide application where freezing of tissues and components have not been suitably rapid in the past, including but not limited to:
   a. Freeze-preservation of living tissues for later revival;
   b. Freeze-fracture of tissues and specimens for study of cleavage planes;
   c. Freeze-fixation of tissues to be studied by microscopic, electron microscopic, auger electron, and X-ray analysis techniques and radioautography;
   d. Rapid freezing wherever the rate of freezing desired is great and objecto to be frozen is too large for direct immersion and rapid agitation in a bath of coolant.

SUMMARY OF INVENTION

The device is a container or reservoir which holds a quantity of liquified hydrocarbon, substituted hydrocarbon, or other material which is liquid at low temperatures, in pure form or in combination, such that the liquid can be dispensed as a liquid or slush from an orifice in order to rapidly cool an object or a portion of the surface of an object as rapidly as possible. Since the liquid or slush is at or near its freezing temperature, it will be able to cool the object surface without itself vaporizing, and since it is a liquid in motion, it will rapidly replace itself so that the specimen surface can be held at or near the melting temperature of the fluid or slush.

It is important that a quenchant be chosen, for spraying onto the specimen, which has a melting point low enough to achieve the desired rapid freezing while preventing ice crystal formation. Preferably the melting point is below $-80°$ C., and, most preferably, as close as possible to or below the boiling point of liquid nitrogen. It is also important, in order to achieve the advantages of the present invention, that the temperature difference between the melting point and the boiling point of the quenchant be about 60°–80° C. This permits the quenchant to remain liquid and avoid the envelope of gaseous insulation, thus permitting fast, efficient cooling. The preferred quenchants are propane and carbon tetrafluoride. Other hydrocarbons, substituted hydrocarbons, such as fluorinated hydrocarbons, or other materials may also be used which fit the above parameters. These include Freon 13 (chlorotrifluoromethane) and 14 (tetrafluoromethane), 1-pentene and 1-butene.

The temperature of the quenchant should be maintained as close as possible to its melting point, such as within 10° C. of the melting point. It is also possible to maintain the liquid at its melting point so that it is sprayed in the form of a slush i.e., a solid-liquid two-phase system. For many applications slush may indeed provide superior results. When a slush is to be maintained the quenchant container may be equipped with apparatus, such as a stirring device, to maintain the liquid in a slush state.

The method of distribution from the container is according to existing art, and can be by liquid withdrawal from the bottom of the container by pressurizing the container, by pumping the fluid, or by a movable piston within the container, so that the liquid is dispersed as a continuous laminar stream or as a spray or disjoint spurting fluid, according to the nature of the object to be frozen.

The orifice of the container is according to existing art, and can be made replaceable so that different sizes of nozzle will provide the type of fluid stream which is desired for the particular freezing application.

In a particularly advantageous embodiment of the present invention, the contact of the liquid stream or spray with the object can be prevented until the nozzle is precooled by the stream of liquid and all gases are cleared from the device. This may be accomplished by means of a deflector or shutter which is per se according to existing art, but which is designed to operate rapidly on activation so that the full jet or stream can rapidly contact the object surface when it is cold enough. Contact may also be avoided by means of starting the stream while the entire device or the nozzle is clear of the specimen, so that the stream is made to contact the specimen only after precooling is accomplished.

The object holder is according to existing art, and may incorporate a rapid means of moving the object to a refrigerator or to a bath of refrigerant as soon as the jet stream has accomplished its action. The object and orifice may be contained within a suitable chamber so that the quenchant fluid is not lost, and so that if a potentially flammable quenchant such as a hydrocarbon is used, it may be totally contained and saved. The object itself may be held in a small or thinwalled container, which container is cooled by the stream to thereby cool the specimen.

The present invention is particularly suitable for use in cooling or freezing relatively large objects, particularly those over 0.5 mm in the largest dimension. While smaller objects have been effectively frozen by prior art techniques, larger objects have presented problems. By the present method and apparatus, the jet stream can be directed at only a small point in a large sample to freeze the area to be studied. Furthermore, samples of unusual shape can be treated without difficulty. For example, specimens such as corneal endothelium which have a concave shape and which must be maintained whole for physiological reasons can be effectively frozen for electron microscopic examination by means of the present invention.

The present invention can also be used to cool objects being heated such as by irradiation or laser.

BRIEF DESCRIPTION OF THE DRAWINGS

Various features of the invention will be apparent from the following detailed description of certain preferred systems embodying various features of the invention when read in conjunction with the accompanying drawings wherein:

FIG. 5 is a schematic diagram of a preferred embodiment of a timer circuit for electronic control of the apparatus represented in FIG. 2.

FIG. 6 is a diagram to show the control operations and their temporal order in the operation of the apparatus represented in FIG. 2 as facilitated by the timer in FIG. 5.

DETAILED DESCRIPTION OF PREFERRED EMBODIMENTS

Figure 1:
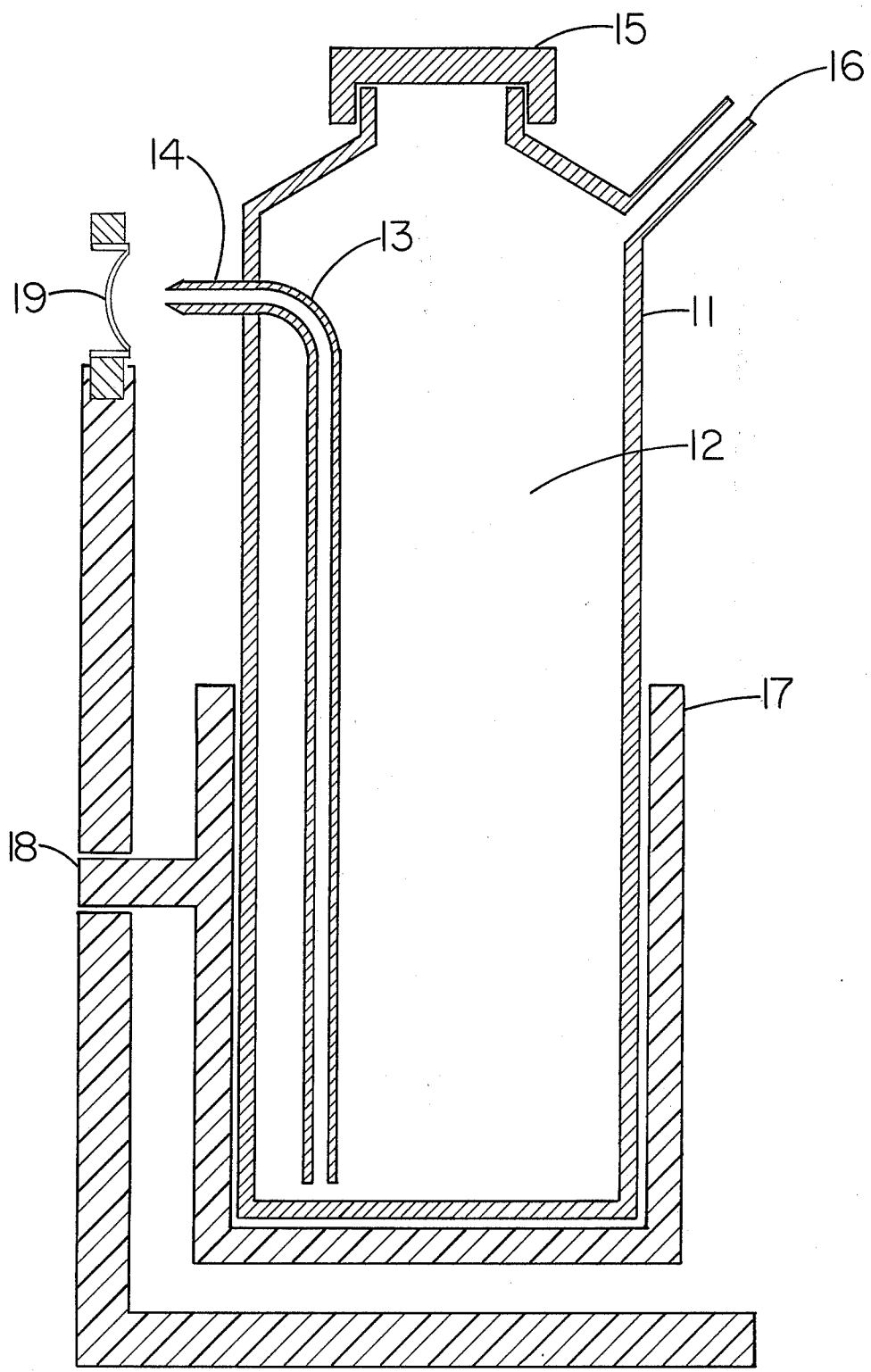
FIG. 1 is an axial cross sectional view of a simple container for dispensing quenching fluid, and a holder to position it with respect to an object to be frozen.

Illustrated in FIG. 1 is an apparatus for the dispensation of quenching fluid including a reservoir 12 to receive quenching fluid, a syphon-type liquid withdrawal system 13, a nozzle 14 for delivery of fluid, a cap 15 affixed by mechanical means or soldering, and an intake port 16 which can be used for pressurization in order to accomplish the delivery of the quenching fluid. The reservoir 12 can be constructed of metal or like material, and brass is found to be a suitable material on account of its rapid heat conduction allowing the container to be cooled rapidly in a bath of liquid nitrogen or the like while it is being filled with quenchant liquid either through the cap 15 or through the syphon tube 13, or through an accessory port. If port 16 is used for filling, gases must be allowed to escape or the liquid will empty through the syphon tube 13. The holder 17 for the reservoir 12 can be made of plastic or the like and designed with a pivot 18 so that the stream of liquid first does not strike the specimen 19 but rather avoids it while the stream cools the nozzle 14 and also pushes gases out of the syphon tube 13. When the liquid stream is precooled, the holder then is made to pivot so that the nozzle 14 is brought into register with the specimen 19. The most rapid freezing or cooling of the object specimen is then accomplished. The illustrated specimen 19 is a mammalian cornea which has been mounted by a pre-existing technique for the freeze fixation of its concave posterior endothelial surface.

Figure 2:
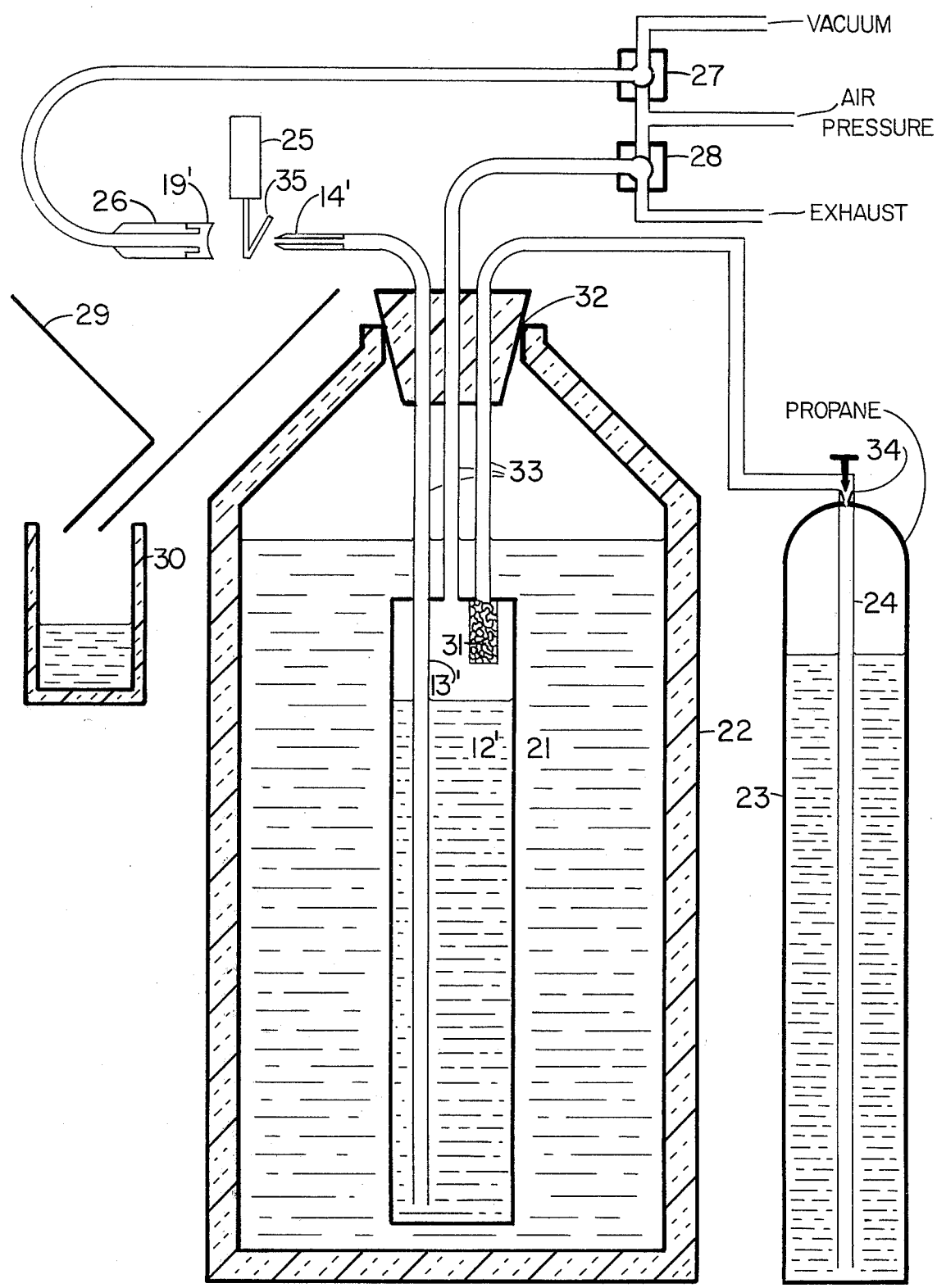
FIG. 2 is a diagrammatic axial cross sectional view of a preferred embodiment of a complete apparatus for the storage and dispensation of quenching fluid with primed numbers corresponding to similar features represented in FIG. 1.
Figure 3:
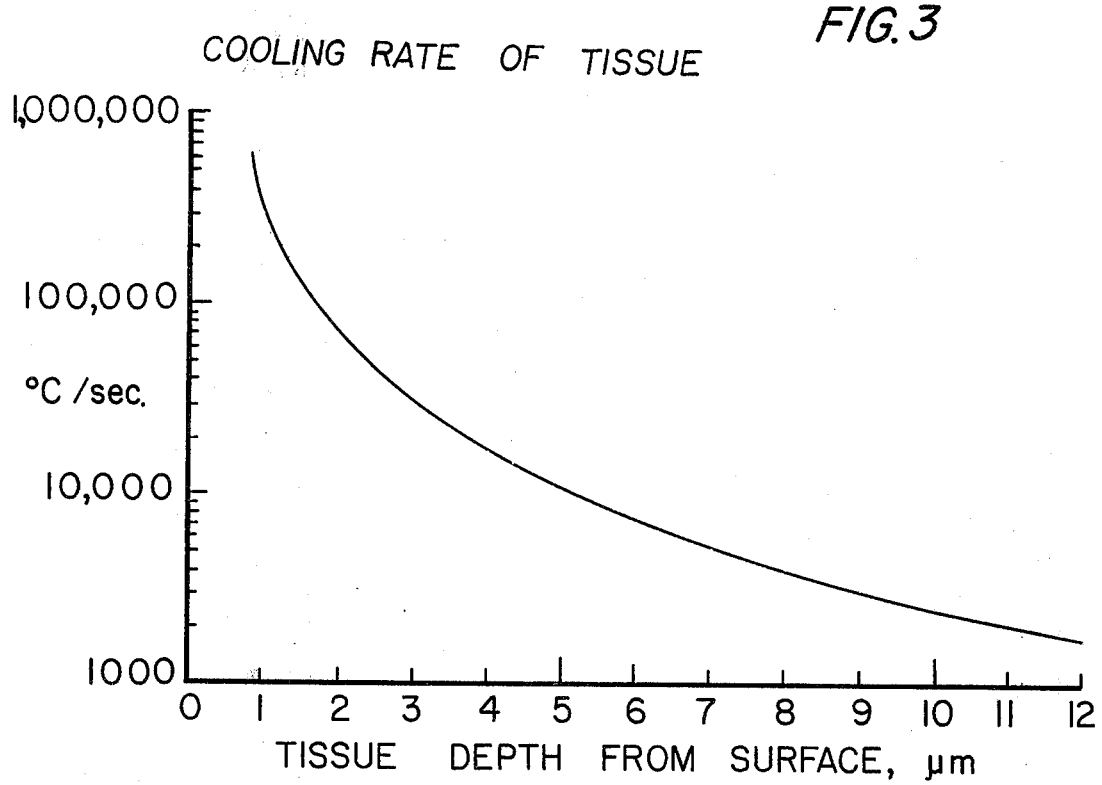
FIG. 3 is a theoretical diagram showing maximum cooling rate of tissue if the surface is immediately and permanently cooled by 200° C.
Figure 4:
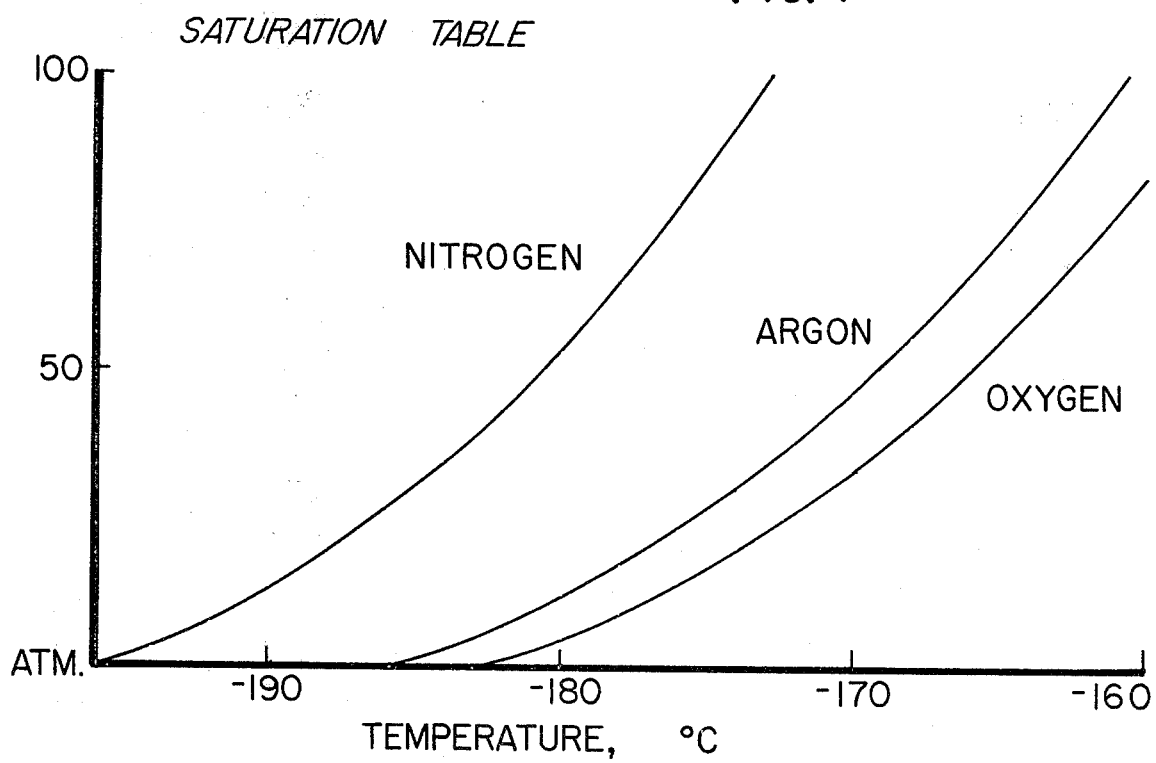
FIG. 4 is a vapor saturation table for some commonly used cryogenic refrigerants, to determine what pressures (gauge) will produce desired temperatures for cooling of quenchant reservoirs.

FIG. 2 illustrates a preferred embodiment of the device wherein a reservoir 12' is stored directly in a Dewar container 22 filled with a suitable freezing agent 21 such that the quenchant liquid is not frozen solid nor is it too warm for optimal freezing or cooling of the sample 19'. Propane stored in liquid argon, or carbon tetrafluoride stored in liquid oxygen, meet these requirements. When a cooling liquid is too cold at atmospheric pressure to prevent freezing of the chosen quenchant liquid, the cooling liquid can be contained at pressure sufficient to raise its saturation temperature to the required level. FIG. 4 is provided to aid in determining the pressure required to achieve proper temperature when cooling with liquid nitrogen, argon or oxygen. The quenchant liquid can be delivered from a tank through a syphon tube 24 into the apparatus where a phase separator and heat exchanger 31 of sintered bronze or the like can facilitate filling of the reservoir 12 (see Wilson, U.S. Pat. No. 3,206,939). Fluid level detection and shutoff can be accomplished by known means.

During filling, gases can be exhausted through three-way valve 28 to the atmosphere, and in the case of flammable quenching liquids such as propane this exhaust can occur away from the apparatus and away from sources of ignition. During filling, the cooling liquid 21 will boil off, and its escape must be provided for by venting insulating cap 32, which should nevertheless not allow free exchange with atmospheric gases, to avoid condensation of carbon dioxide and concentration of oxygen. Where Dewar container 22 is of sufficiently high vacuum and baffling to provide very slow heat leakage from the device, best economy of operation will prevail. Likewise pipes 33 should be of a good insulator such as nylon or polyethylene tubing, and may be of a 300 series stainless steel, but should not be of brass or copper and must not be of embrittling material such as series 400 stainless steel.

A timing device to accomplish the various and necessary steps of the freezing may be used, and one possible embodiment of the device is shown in FIG. 5. The timing steps which are useful are illustrated by diagrammatic means in FIG. 6, and include starting of the jet stream, a delay period to allow precooling of the nozzle, shutter opening after precooling, a freezing period of jet pressure long enough to allow the container to expel its contents or enough thereof to allow adequate cooling of the object, closure of the shutter, stopping of the jet stream, and ejection of the object to a receiving device for total cooling and storage.

During the process of freezing, valve 34 is closed, and three-way valve 28 is switched to apply air pressure to reservoir 12, forcing fluid to flow through syphon tube 13' and cool nozzle 14'. Deflecting shutter 35 directs the liquid stream through a collecting funnel to an insulated reservoir 30 while the liquid stream attains desired cold temperature. Shutter 35 is then retracted or opened by device 25 which can be a solenoid electrically controlled, and fluid stream freezes or cools specimen 19'. After freezing is accomplished, shutter 35 is again closed, and the specimen 19' can be quickly removed to reservoir 30 or another storage refrigerator. One means of accomplishing this is by switching three-way valve 27 from vacuum to the air pressure source so that specimen 19' is ejected from its holder 26 and collected by funnel 29. Since only the single surface of specimen 19' is frozen, freezing of the entire specimen should be accomplished at this time, which will be accomplished by its immersion in the fluid collected in reservoir 30. Used quenchant fluid stored in container 30 may then be returned to container 21 for reuse as taught by Damsz (U.S. Pat. No. 3,206,938, or Bentz (U.S. Pat. No. 4,059,424).

FIG. 5 illustrates a preferred embodiment of an adjustable timer circuit which can be used to regulate the device shown in FIG. 2. The timers IC 1, IC 2, IC 3, and IC 4 can be 555 integrated circuits or the like, and the relays controlled by IC 1, IC 3, and IC 4 in turn control the jet pressure three-way valve 28, the shutter solenoid 25, and the three-way ejector valve 27 of the device illustrated in FIG. 2. A trigger pulse arriving at pin 2 of IC 1 starts timing sequences in IC 1 and IC 2, IC 2 then triggers IC 3, and IC 1 triggers IC 4.

FIG. 6 illustrates schematically the timing sequence as embodied by the timers in FIG. 5. The trigger pulse starts the jet pressure or pumping, and a delay timer which allows precooling of the tissue. The shutter then opens, and closes at the time that the reservoir is emptied. The eject relay then transfers the specimen to a cold storage chamber for further processing. A refill circuit not illustrated then can control filling of the reservoir chamber with more quenchant, or the spent quenchant can be pumped back into the chamber for reuse.

While the above description contains many specificities, these should not be construed as limitations on the scope of the invention, but rather as an exemplification of one preferred embodiment thereof. Many other variations are possible, for example inclusion of freezing coils and apparatus for the cooling of the quenchant fluid. Accordingly, the scope of the invention should be determined not by the embodiment illustrated, but by the appended claims and their legal equivalents.

What is claimed is:

1. A process for rapid freezing of at least a portion of the surface of an object, comprising:
   supplying a stream of quenchant cooled to, or close to, the freezing point thereof, said quenchant having a freezing point below about $-80°$ C. and a temperature difference between the melting point and the boiling point thereof of more than about 60° C.; and directing said stream at the surface to be frozen.

2. A process in accordance with claim 2, further including the step of, prior to said directing step, permitting said stream of quenchant to flow, without being directed at the tissue surface to be frozen, until the temperature of said stream substantially stabilizes.

3. A process in accordance with claim 2, wherein said quenchant is stored in a reservoir having a nozzle and said supplying step comprises causing the quenchant to flow from said reservoir and through said nozzle.

4. A process in accordance with claim 3, wherein said reservoir is maintained at the desired temperature by a suitable freezing agent.

5. A process in accordance with claim 4, wherein said quenchant is propane and said freezing agent is liquid argon.

6. A process in accordance with claim 4, wherein said quenchant is carbon tetrafluoride and said freezing agent is liquid oxygen.

7. A process in accordance with claim 4, wherein said freezing agent is a liquefied gas under superatmospheric pressure.

8. A process in accordance with claim 3, wherein said quenchant is propane, carbon tetrafluoride, chlorotrifluoromethane, 1-pentene or 1-butene.

9. A process in accordance with claim 1, wherein said stream of quenchant is cooled to a temperature below about 10° C. above the freezing point thereof.

10. A process in accordance with claim 1, wherein the temperature difference between the melting point and the boiling point of the quenchant is about 60° to about 80° C.

11. A process in accordance with claim 1, wherein said stream of quenchant is in the form of a solid-liquid two-phase slush.

12. A process in accordance with claim 1, wherein the object at which the stream is directed is over 0.5 mm in the largest dimension.

13. A process in accordance with claim 1, wherein the reservoir is maintained at the desired temperature by means of mechanical cooling means including cooling coils.

14. An apparatus for rapid freezing of at least a portion of the surface of an object, comprising:
   a reservoir for the storage of fluids at temperatures below about $-80°$ C.;
   a nozzle connected to said reservoir through which fluid or slush stored in said reservoir can be withdrawn;
   withdrawal means for causing the fluid or slush stored in said reservoir to flow through said nozzle;
   holding means for holding the object, the surface of which is to be frozen; at a position at which fluid or slush flowing through said nozzle can come into direct or indirect contact therewith; and
   delay means for automatically preventing fluid or slush flowing through said nozzle from contacting the object held by said holding means until the fluid or slush has passed through said nozzle for a time sufficient to reach the desired temperature.

15. An apparatus in accordance with claim 14, wherein said holding means holds the object in a small or thinwalled container to be cooled by the stream.

16. An apparatus in accordance with claim 14, wherein said delay means comprises a shutter means for deflecting the flow of fluid or slush from contact with the object when in a first position and for permitting flow of fluid or slush to come into contact with the object when in a second position, and timing means for automatically initiating flow of fluid or slush by means of said withdrawal means and movement of said shutter means from said first to said second position after a predetermined time.

17. An apparatus in accordance with claim 14, further including stirring means for maintaining the contents of said reservoir in the form of a two-phase solid-liquid slush.

* * * * *